(12) United States Patent
Bighouse et al.

(10) Patent No.: US 6,424,409 B1
(45) Date of Patent: Jul. 23, 2002

(54) METHODS AND APPARATUS FOR DETECTING SURFACE DEFECTS OF AN OPTICAL FIBER

(75) Inventors: Roger D. Bighouse, Beaver Dams; David A. Pastel, Horseheads, both of NY (US); Bruce W. Reding, Wilmington, NC (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/445,062

(22) PCT Filed: May 12, 1998

(86) PCT No.: PCT/US98/09811

§ 371 (c)(1),
(2), (4) Date: May 22, 2000

(87) PCT Pub. No.: WO98/53305

PCT Pub. Date: Nov. 26, 1998

Related U.S. Application Data

(60) Provisional application No. 60/047,399, filed on May 22, 1997.

(51) Int. Cl.[7] .............................................. G01N 21/00
(52) U.S. Cl. .................................................... 356/73.1
(58) Field of Search ........................ 356/73.1; 65/382, 65/378, 160, 29.18; 250/461.1, 302

(56) References Cited

U.S. PATENT DOCUMENTS

| 4,236,904 A | | 12/1980 | Lazay |
|---|---|---|---|
| 4,501,492 A | * | 2/1985 | Douklias |
| 4,678,327 A | | 7/1987 | Yoshida et al. |
| 4,924,087 A | | 5/1990 | Bailey et al. |
| 4,929,837 A | * | 5/1990 | Divita et al. |
| 5,185,636 A | | 2/1993 | Button et al. |
| 5,408,308 A | | 4/1995 | Allegretto et al. |
| 5,436,719 A | | 7/1995 | Doles et al. |
| 5,443,610 A | | 8/1995 | Urruti |
| 5,469,252 A | | 11/1995 | Doles et al. |
| 5,472,128 A | | 12/1995 | Nagayama et al. |
| 5,493,123 A | | 2/1996 | Knollenberg et al. |
| 5,519,487 A | | 5/1996 | Atwood et al. |
| 5,551,967 A | * | 9/1996 | Urruti |
| 5,597,398 A | * | 1/1997 | Ishikawa et al. ............... 65/413 |

* cited by examiner

Primary Examiner—Frank G. Font
Assistant Examiner—Tu T. Nguyen
(74) Attorney, Agent, or Firm—Timothy R. Krogh

(57) ABSTRACT

An optical fiber flaw detection apparatus for detecting white light emitted through a sidewall of an optical fiber and methods of detecting the flaw are disclosed. One embodiment of the apparatus includes a detector located adjacent the fiber and processing circuitry to amplify and convert a signal produced to recognize flaws. A second embodiment includes a plurality of view systems oriented about the fiber and a mechanism to rapid draw fiber through the systems in addition to the detector. Each system is an optical assembly for collecting and directing the light. One method includes the steps of introducing the light into the fiber, detecting the light, and determining on-line the nature of the flaw. A second method includes the steps of heating a preform to a temperature sufficient to draw fiber, drawing fiber, and detecting the emitted light. The draw temperature is sufficient to transmit the light along the fiber.

36 Claims, 8 Drawing Sheets

METHODS AND APPARATUS FOR DETECTING SURFACE DEFECTS OF AN OPTICAL FIBER

This application claims benefit of provisional application No. 60/047,399 filed May 22, 1997.

FIELD OF THE INVENTION

The present invention relates generally to quality control in the production of optical fiber and the early detection of optical fiber defects. More particularly, the invention relates to a photodetection system and methods for the detection of flaws and surface defects, such as those caused by particles adhering to the surface of an optical fiber during its manufacture.

BACKGROUND OF THE INVENTION

During the drawing of an optical fiber from a blank, various imperfections may occur. These imperfections include holes in the fiber, inclusions or particles within the fiber, particles on the surface of the fiber, and surface abrasions. The presence of surface abrasions and of particles on the fiber can cause the fiber to break at later stages of manufacture. Thus, quality control is critical during the manufacture of optical fiber both from the point of view of achieving the highest possible manufacturing yield. To this end, a variety of techniques for testing the quality of optical fibers are known. For example, tension screening of fiber may be performed off-line some time after manufacturing is completed. Defects or flaws result in fiber breakage. None of the presently existing techniques addresses the on-line real time detection of surface particles as optical fiber is drawn or manufactured.

SUMMARY OF THE PRESENT INVENTION

The ability to detect particles on the optical fiber as it is drawn would be beneficial as both a process improvement tool and by providing the information necessary to reduce the number of particle induced breaks occurring later in the fiber optic manufacturing process. By way of example, real time detection of a large increase in the number of flaws might indicate that the furnace refractories are deteriorating and the furnace should be replaced.

The present invention recognizes that a fiber optic perform and a drawn fiber including the cladding prior to its coating form excellent waveguides. As such, light permeates substantially the entire cross section of the fiber prior to coating. The majority of the light is guided down the entire length of the fiber unless scattered out along the length of the fiber by an imperfection, such as a hole, surface abrasion, or particle. During the drawing process, optical fiber is filled with light in the draw furnace which is an excellent source of intense white light. As the fiber is drawn, light from the draw furnace is conducted along it and scattered out as a result of imperfections. Because of the speed at which the fiber is moving as it is being drawn, the scattered light will be seen by a detector as a brief flash as the defect rapidly passes the detector.

Among the other needs addressed by the present invention is the need for a detector which can detect flashes caused by scattering of light due to imperfections in an optical fiber as the fiber is being drawn. The present invention also provides a detector which can operate effectively at the normal speed at which optical fiber is drawn to identify a flash caused by the presence of a particle on the surface of the optical fiber. Such particles may be referred to herein as particles on glass or POGs.

One aspect of the present invention preferably comprises a high speed large area detector placed at one focal point of an elliptical mirror. The optical fiber to be subjected to detection is placed at the other focal point of the mirror. The mirror arrangement provides that 180 degrees of the light scattered from the fiber will be reflected onto the detector. The detection components are preferably shielded to block out stray light and purged with an inert gas to keep their optical surfaces clean.

According to another aspect of the invention, an elliptical mirror is used. The fiber is placed at one focal point of the mirror and a fluorescent rod which preferably has a diameter of 1 cm is placed at the other focal point. The rod preferably has polished ends and is oriented parallel to the fiber. One end of the rod is preferably mirrored, while a high speed Silicon detector is attached to the other end. The rod is doped with a fluorescent dye which absorbs visible light, preferably yellow light, and fluoresces in the visible or near IR part of the spectrum. As the light from the fiber hits the rod, fluorescence will occur. Approximately half of the light will fluoresce out of the rod and be lost. One quarter of the light will be guided inside the rod, reflect off the mirrored surface and then be guided back down to the detector, while the remaining quarter of the light will be guided directly to the detector. Fluorescence occurs very fast, on the order of 10 ns, so even very fast flashes may be readily detected. Also, since the rod has a diameter of 1 cm, all of the light scattered from the fiber will hit the rod and the system will be insensitive to fiber movement. Further, it will be recognized that by increasing the length of the rod the time during which a flash will be observed will be increased. Additionally, the rod may be preferentially masked to distinguish between particles and holes, for example.

Another aspect of the present invention preferably comprises a two-view system. Each view includes a small area, high-speed, sensitive Silicon detector, two lenses, and a spherical mirror. The lens system makes the view less sensitive to fiber movement. In the preferred embodiment of the invention, lenses are used which allow the system to tolerate fiber movement of 2.5 mm.

The lenses are placed on one side of the fiber, and the spherical mirror is placed on the other side of the fiber at its radius of curvature away from the fiber. All the incident light from the fiber is thus reflected back to the detector. Using two views spaced 90 degrees apart increases the likelihood that a flash from a POG will be collected. Also, it is believed that signal differences between the detectors may be used to discriminate particle type and hole presence given the addition of suitable signal processing support to rapidly analyze the signal differences. The system is preferably housed in a box to block out stray light and purged with an inert gas. The housing will preferably be mounted on adjustable x and y stages to properly locate the detector with respect to the fiber. A source of purge gas will be supplied to keep the optical surfaces of the detector contamination free.

Another aspect of the invention preferably comprises a three-view system. Each view includes a small area, high-speed, sensitive Silicon detector, three lenses, and a spherical mirror. The lenses are placed on one side of the fiber, and the spherical mirror is placed on the other side of the fiber at its radius of curvature away from the fiber. All the incident light from the fiber is thus reflected back to the detector. Using three views spaced 120 degrees apart eliminates any dead zone in which the fiber can be present without a flash being detected. The use of three views and three lenses permits a detector according to this aspect of the invention to detect flashes at high speeds, such as typical draw speeds used during optical fiber manufacturing, given the proper selection and configuration of parts. Further, while a variety of approaches are described in detail, it will be recognized that multiple view systems may be employed with the number of views determined by the application and considerations such as cost. Various other optical arrangements and detectors may be suitably employed.

A more complete understanding of the present invention, as well as further features and advantages of the invention, will be apparent from the following Detailed Description and the accompanying drawings.

DETAILED DESCRIPTION

Figure 1:
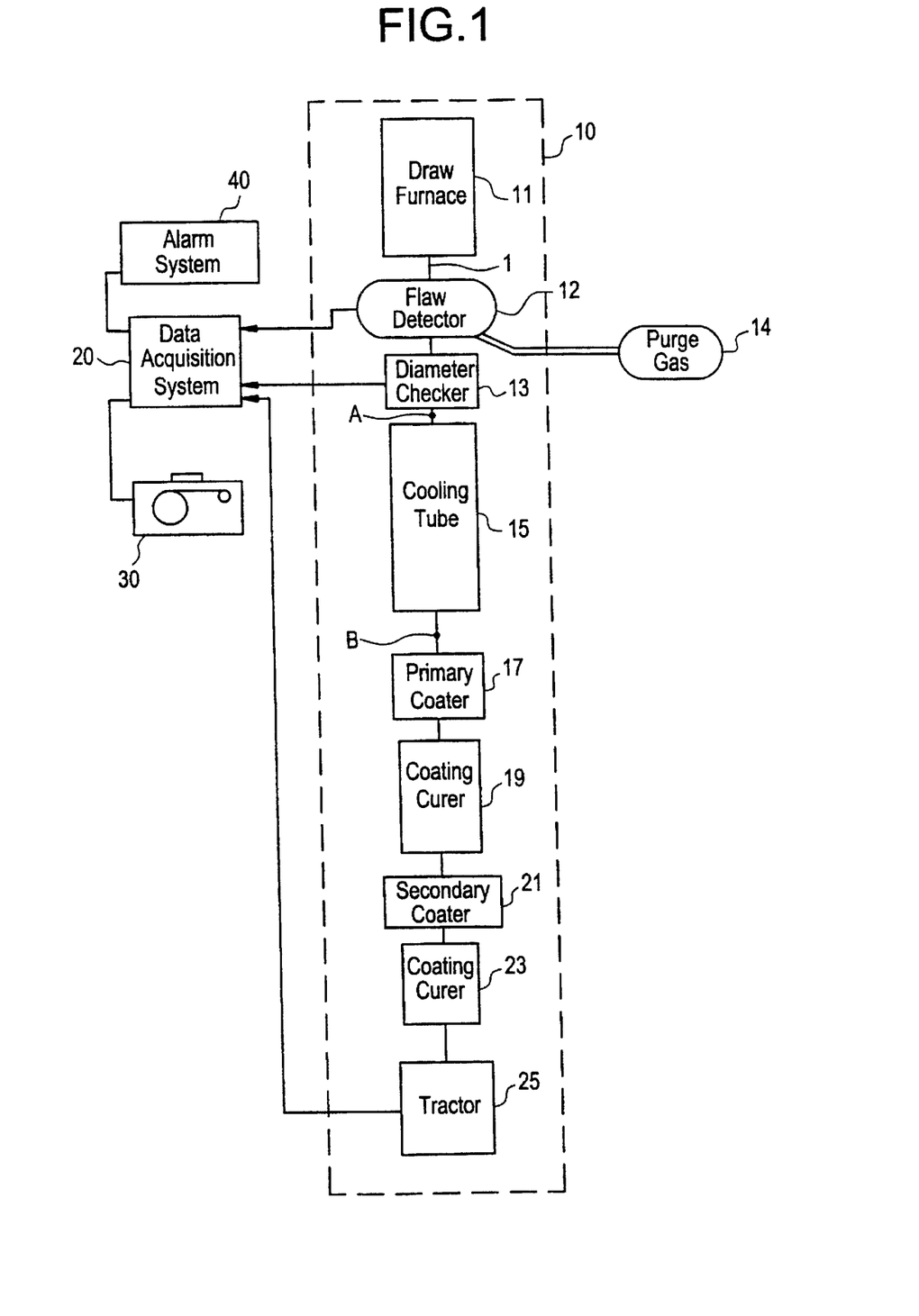
FIG. 1 illustrates an optical fiber draw process and system according to the present invention.

FIG. 1 illustrates an optical fiber draw process and system 10 employing optical fiber flaw detection in accordance with the present invention. In the system 10, an optical fiber 1 is drawn from a draw furnace 11 which preferably heats to the fiber to a temperature of approximately 1900–2000° C. This temperature is sufficiently hot to cause the fiber to glow and to be substantially filled with white light. As the fiber 1 leaves the draw furnace 11, it passes through a flaw detector 12 which will preferably be constructed in accordance with the principles described further below in conjunction with the discussion of FIGS. 2A–7 although it will be recognized that other optical detection arrangements and housings may be suitably devised consistent with the teachings and claims which follow. The flaw detector 12 is preferably located directly after the draw furnace 11 as at this point in the process substantially all surface abrasions have been eliminated by the high heat of the draw furnace 11. However, it will be recognized that the flaw detector 12 may also be located at points, such as the points A or B located after the diameter checker 13 or the cooling tube 15 as shown in FIG. 1, or alternatively might be combined with the diameter checker 13 to form a dual function single housing unit if desired.

Next, the fiber 1 passes through a diameter checker 13 which checks the diameter of the fiber 1 in a known fashion. The diameter checker 13 may suitably be an interference diameter measurement ("IDM") device such as those described in U.S. Pat. No. 5,309,221 which is assigned to the assignee of the present invention and which is incorporated by reference herein in its entirety. From the diameter checker 13, fiber 1 then passes a cooling tube 15, a primary coater 17, a first coating curer 19, a secondary coater 21, a second coating curer 23 and a tractor 25. The tractor 25 provides the appropriate force to draw the fiber 1 at the desired process speed. Further details of one existing draw system are described in U.S. Pat. No. 5,443,610 which is assigned to the assignee of the present invention and incorporated by reference herein in its entirety.

In addition to the above described components, system 10 also includes a source of purge gas 14 which provides gas to purge the optical surfaces of the flaw detector 11 to prevent such surface from becoming contaminated. System 10 also includes a data acquisition system 20, a chart recorder 30 and an alarm system 40. The data acquisition system 20 will preferably include fast digital signal processing circuitry to amplify, convert and process the signal produced by the flaw detector 12. A PC, workstation or minicomputer including a suitably programmed controller, memory, a display, a keyboard, and printer may suitably be included. By connecting the data acquisition system 20 to the flaw detector 12, the diameter checker 13 and the tractor 25, holes can be discriminated from other flaws such as POGs as the IDM can be employed to detect holes in a known fashion, for example, as described in U.S. Pat. No. 5,185,636 which is assigned to the assignee of the present invention and incorporated by reference in its entirety. The data acquisition system 20 can monitor and check the draw speed at the fiber 1. The chart recorder 30 can be employed to keep a log of the location of various flaws along the optical fiber 1. Alarm system 40 may be employed to provide appropriate alarms to manufacturing process control personnel or a control processor in response to real time flaw detection.

Figure 2A:
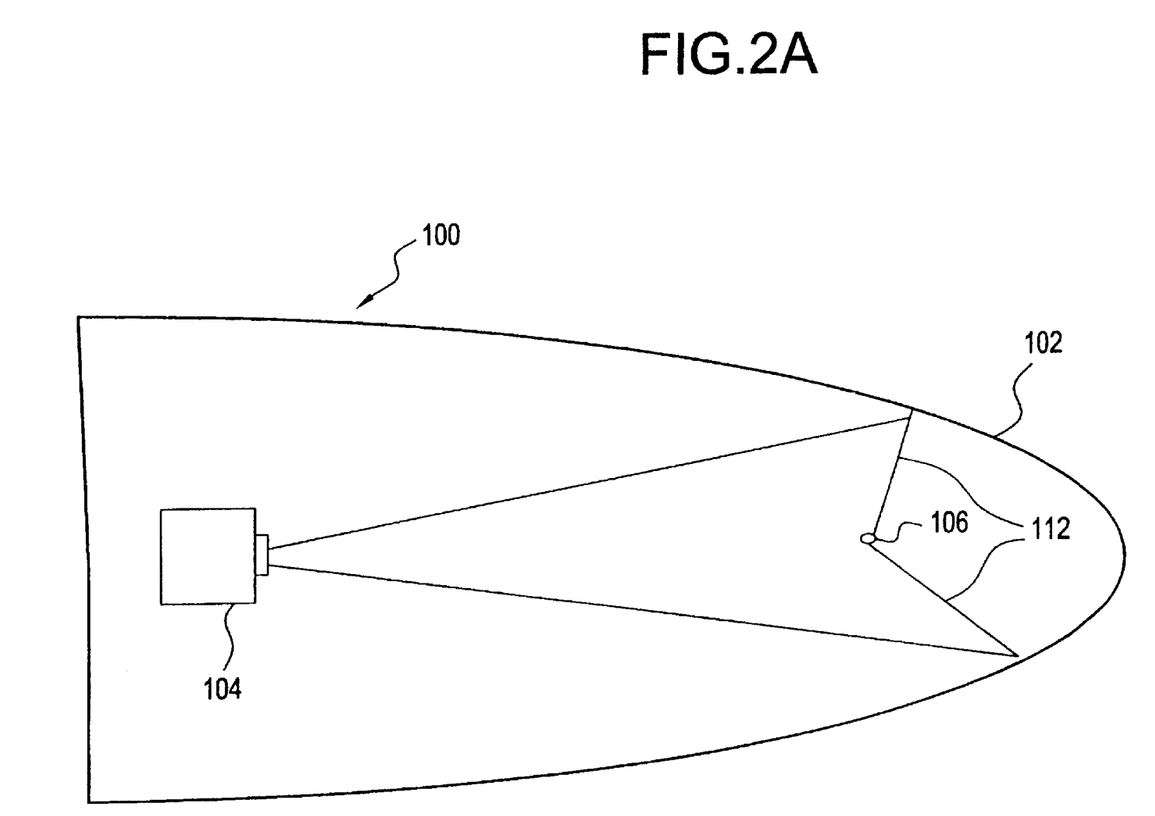
FIG. 2A illustrates a top view of a flash detection system comprising an elliptical mirror and a detector according to the present invention.

FIG. 2A illustrates a top view of a flash detection system 100 according to one aspect of the present invention. This system 100 may suitably be employed as the flaw detector 12 of FIG. 1. Detection system 100 comprises an elliptical mirror 102 and a detector 104. The detector 104 is placed at one focal point of the mirror 102. An optical fiber 106 is introduced between detector 104 and mirror 102 at the other focal point of the mirror 102. As seen in FIG. 2A, the optical fiber 106 is traveling down into the page. Light is normally conducted through the fiber 106 without exiting the fiber 106. An irregularity on the surface or other flaw of the fiber 106, however, will cause light 112 to escape from the surface. Such an irregularity is most often a particle on glass, or POG, adhering to the surface of the fiber 106. Light 112 will escape from the fiber 106 at the POG. About 180 degrees of the light 112 will strike the mirror 104 and be reflected onto the detector 104.

Figure 2B:
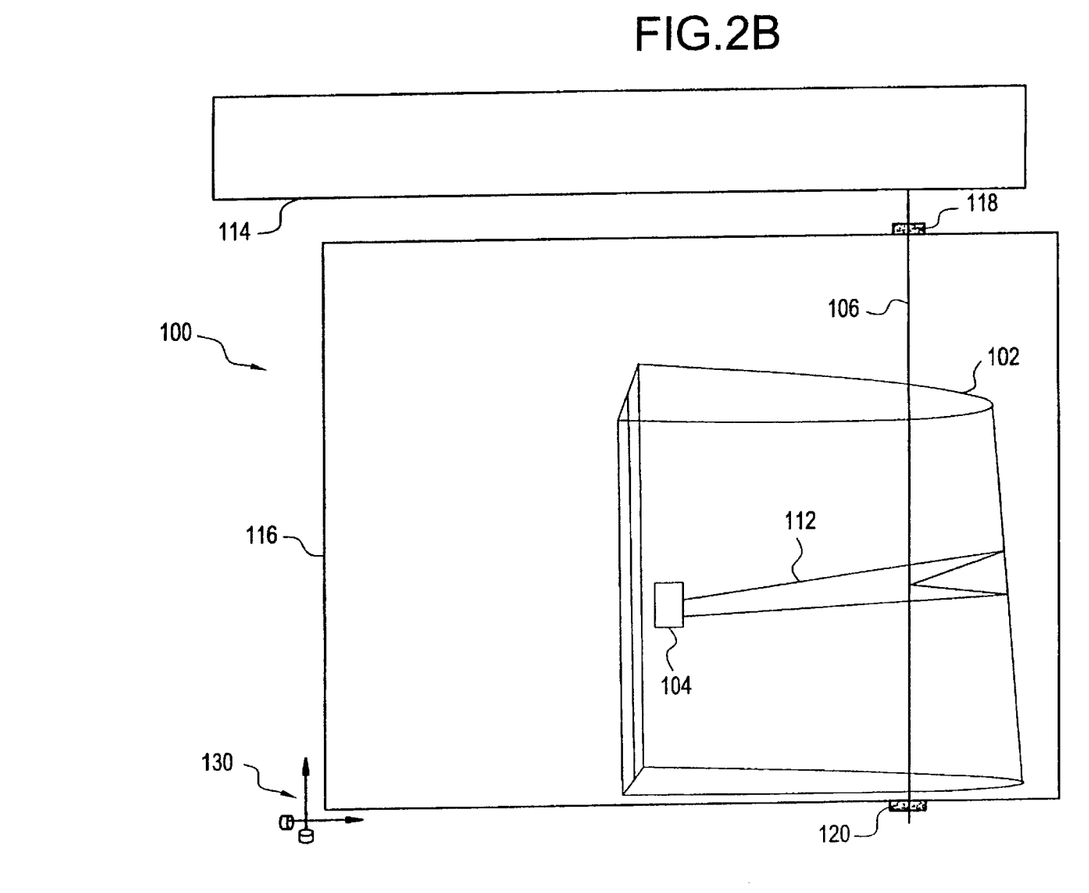
FIG. 2B illustrates a side view of the flash detection system of FIG. 2A.

FIG. 2B illustrates a side view of the detection system 100, with a fiber 106 being fed into the detection system 100 from a furnace 114, and providing additional views of the mirror 102, the detector 104, and the fiber 106. FIG. 2B also illustrates an enclosure or housing 116 in which detector 100 is suitably enclosed to prevent the entry of ambient light. Baffles 118 and 120 provide additional shielding from ambient light at the points where the fiber 106 enters and exits the housing 116. Additionally, x and y translation stages 130 may be suitably employed to manually or automatically adjust the position of the mirror 102 with respect to the fiber 106.

Detector 100 may be advantageously used during the drawing of fiber 106. Fiber 106 can be fed into detector 100 as it is drawn from the furnace 114 where that furnace is a draw furnace such as the draw furnace 11 of FIG. 1. The furnace 114 heats the perform from which fiber 106 is drawn white hot. This heating results in intense white light being conducted within the fiber 106.

Because the fiber 106 and the detector 104 are at the opposite foci of the elliptical mirror 102, the detector 100 according to the illustrated aspect of the invention is sensitive to movement of the fiber 106. Movement of the fiber 106 moves the fiber 108 off the focus of the mirror 102, thereby preventing the mirror 102 from precisely focusing the light escaping from fiber 106 onto the detector 104.

Figure 3:
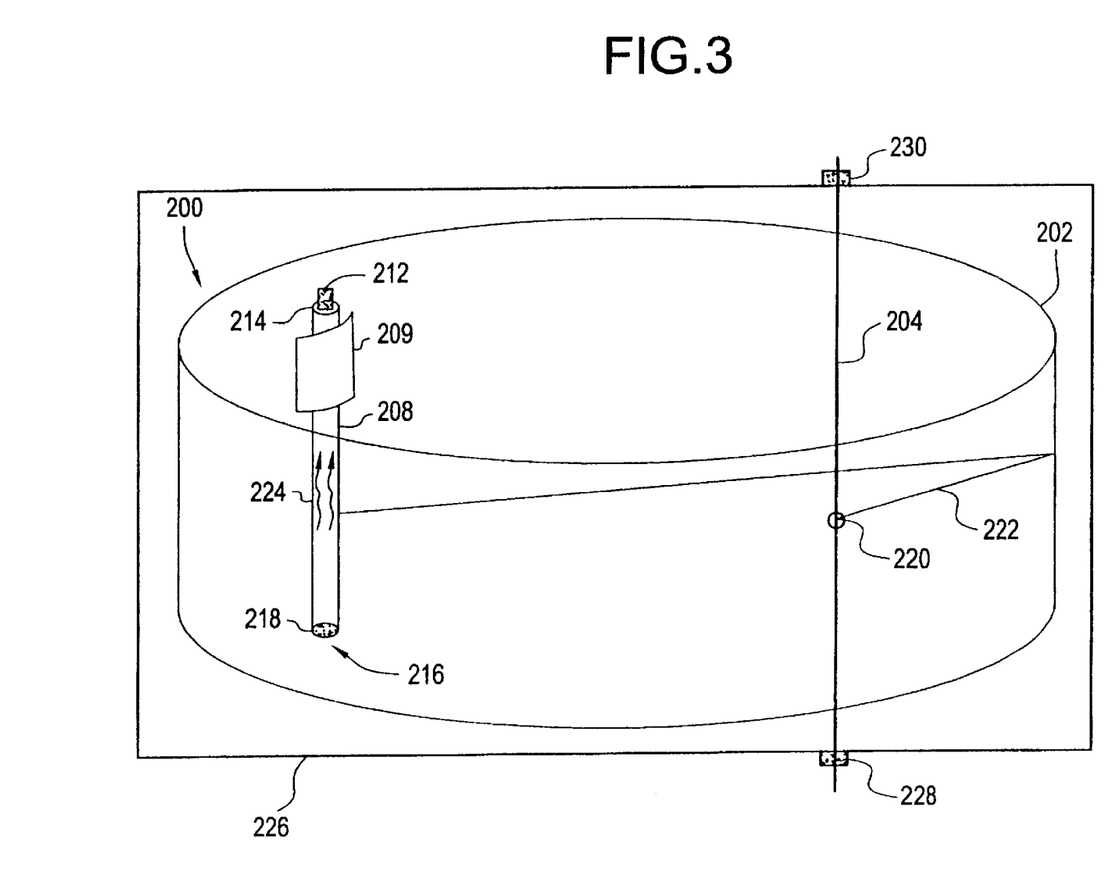
FIG. 3 illustrates a side view of a flash detection system employing an elliptical mirror and a fluorescent rod according to the present invention.

FIG. 3 illustrates a detection system 200 according to another aspect of the present invention. System 200 may also suitably be employed as the flaw detector 12 of FIG. 1. The detection system 200 includes an elliptical mirror 202. Fiber 204 is placed at the first focus of the mirror 202, while a fluorescent rod 208, preferably one centimeter in diameter, is placed at the second focus of the mirror 202. A detector 212 is placed at a first end 214 of the rod 208, while a mirror 216 is placed at the second end 218 of the rod 208. Rod 208 can suitably be of an acrylic or glass material which is doped with a fluorescent dye. The dye preferably absorbs visible light, such as is emitted by the white hot perform, and fluoresces in the visible or near IR region of the spectrum.

Light introduced into one end of the fiber 204 will be transmitted along the length of the fiber 204 until encountering an irregularity 220. Scattered light 222 will then be emitted from the fiber 204 and collected by the mirror 202. A substantial amount of scattered light 222 will then be focused onto the rod 204, which will fluoresce, producing fluorescent light 224. Approximately one half of the fluorescent light 224 will escape from the rod 208 and be lost. About one quarter of the fluorescent light 224 will be guided up the rod 208, reflected by the mirror 216, guided back down by the rod 208, and onto the detector 218. An additional one quarter of fluorescent light 224 will be guided directly down rod 208 to the detector 218. Because of the volume of the rod 208, the detection system 200 is relatively insensitive to movement of the fiber 204. A slight loss of focus of light 222 will not prevent the light 222 from striking rod 208 somewhere. Rod 208 will then produce fluorescent light 224 for detection by the detector 218.

By increasing the length of the rod 208, the observation time of a flash will be increased. Also, the rod may be selectively masked so that it picks up preferential scattering differently. For example, a mask 209 may shield the upper third of the rod 208 from light impinging from a range of angles. It will be recognized that additional masks which are not shown might also be employed. By comparing the signals measured as a flash passes the top third with the signals measured as a flash passes the bottom of the rod 208, it should be possible to distinguish holes from surface particles and it may be possible to distinguish different types of particles if those particles result in preferential scattering.

The detection system 200 may be suitably enclosed in a light-tight enclosure 226 with baffles 228 and 230 at the points where fiber 204 enters and exits the light-tight enclosure 226 in order to prevent the entry of ambient light into light-tight enclosure 226. Purge gas and adjustable stages may be employed as discussed above.

Figure 4:
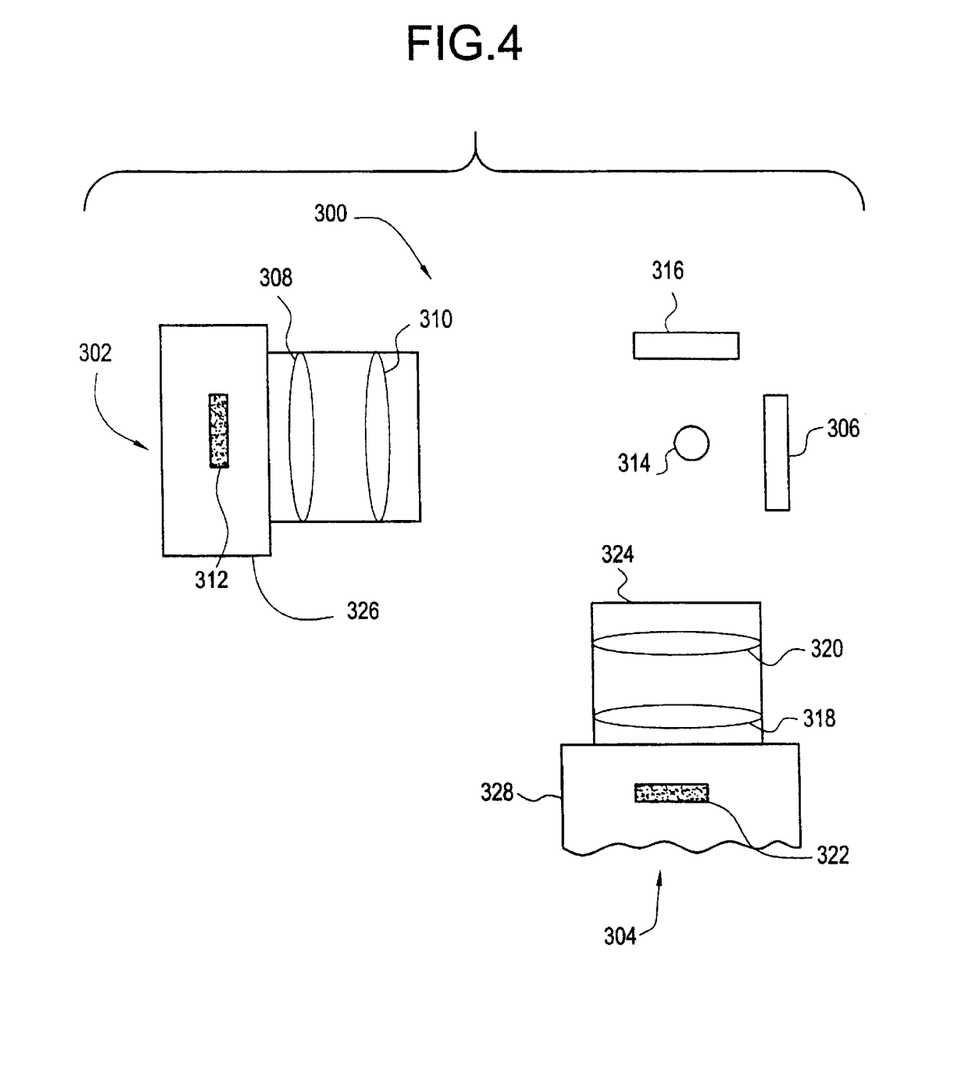
FIG. 4 illustrates a top view of a two-view flash-detection system according to the present invention.

FIG. 4 illustrates a top view of a two-view flash detector 300 according to another aspect of the present invention. Detector 300 may suitably be employed as the flaw detector 12 of FIG. 1. The detection system 300 includes first and second view systems 302 and 304, respectively. While a presently preferred optical assembly is described below, it will be recognized that any other suitable optical assembly may be employed to collect and guide light emitted from the sidewalls of the fiber 314, and direct it to first detector 312.

First view system 302 includes a first spherical mirror 306, first and second lenses 308 and 310, and a first detector 312. Mirror 306 is placed a distance equal to its radius of curvature from fiber 314. Second lens 310 is placed on the opposite side of the fiber 314 from mirror 306, in line with mirror 306, and a distance equal to the focal length of lens 310 from the fiber 314. First lens 308 is placed on the opposite side of lens 310 from fiber 314, in line with mirror 306 and lens 310. First detector 312 is on the opposite side of lens 308 from fiber 314, in line with mirror 306 and lenses 308 and 310, at a distance from lens 308 equal to the focal length of the lens 308. Lenses 308 and 310 are preferably mounted in a lens mount 322. The lens mount 312 is preferably adapted to fit directly into the housing 326 which encloses the detector 312. This arrangement shields detector 312 from ambient light which may have entered the detection system 300.

Second view system 304 includes a second spherical mirror 316, third and fourth lenses 318 and 320, and a second detector 322. The second view system 304 is oriented 90 degrees perpendicular to the first view system 302 and is located in the same plane as the first view system 302. Mirror 316 is located a distance equal to its radius of curvature from the fiber 314. Fourth lens 320 is placed on the opposite side of the fiber 314 from mirror 316, in line with mirror 316, and at a distance from fiber 314 equal to the focal length of the lens 320. Third lens 318 is placed on the opposite side of lens 320 away from the fiber 314, in line with the mirror 316 and the lens 320. Second detector 322 is on the opposite side of lens 318 away from the fiber 314, in line with mirror 316 and lenses 318 and 320, at a distance from lens 318 equal to the focal length of the lens 318. Lenses 318 and 320 are mounted in a lens mount 324, and the lens mount 322 is preferably adapted to fit directly into a housing 328 which encloses the detector 322. This arrangement operates to shield the detector 322 from ambient light.

The detection system 300 is preferably enclosed in a light-tight enclosure having suitable entry and exit points for fiber 314, with baffles shielding the entry and exit points. The light-tight enclosure of detection system 300 is not shown, but may be similar to those described above in conjunction with the embodiments of FIGS. 2B and 3. While it is presently preferred to have the view systems 302 and 304 coplanar, it will be recognized that they may also be arranged so as to be displaced from one another and their outputs may then be processed to analyze for preferential scattering to detect holes and distinguish different types of particles.

It will be recognized that two view and multiple view systems more generally may provide multiple signals simultaneously as the fiber 314 moves past. With appropriate analysis, it may prove possible to analyze differences in such signals to gain further valuable information. For example, it may prove possible to distinguish a hole from a POG, or one type of POG from another.

Figure 5:
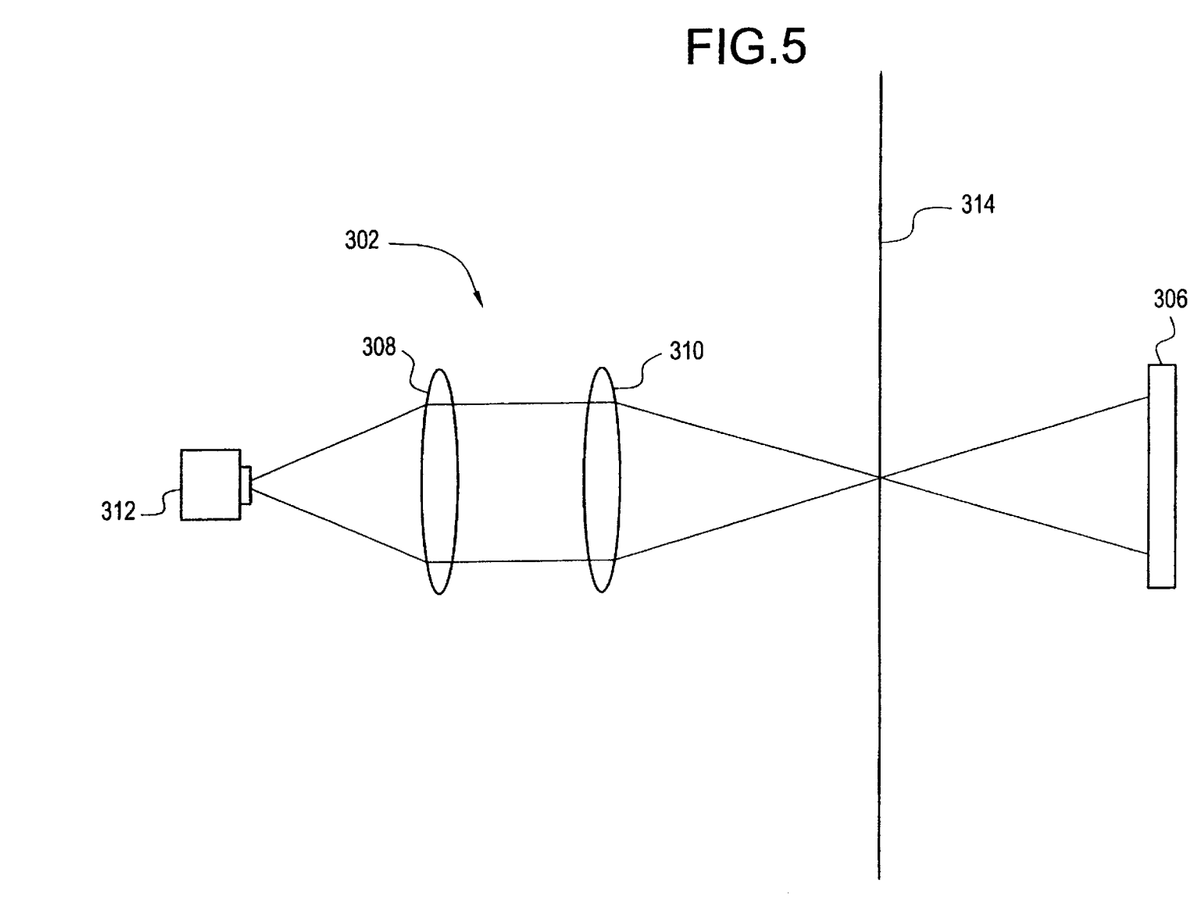
FIG. 5 is a side view of a portion of the two-view flash detection system as depicted in FIG. 4.

FIG. 5 illustrates a side view of the view system 302 of the detector 300. As discussed above, the view 302 includes the mirror 306, first and second lenses 308 and 310, and first detector 312, all oriented in a straight line which intersects the fiber 314.

Figure 6:
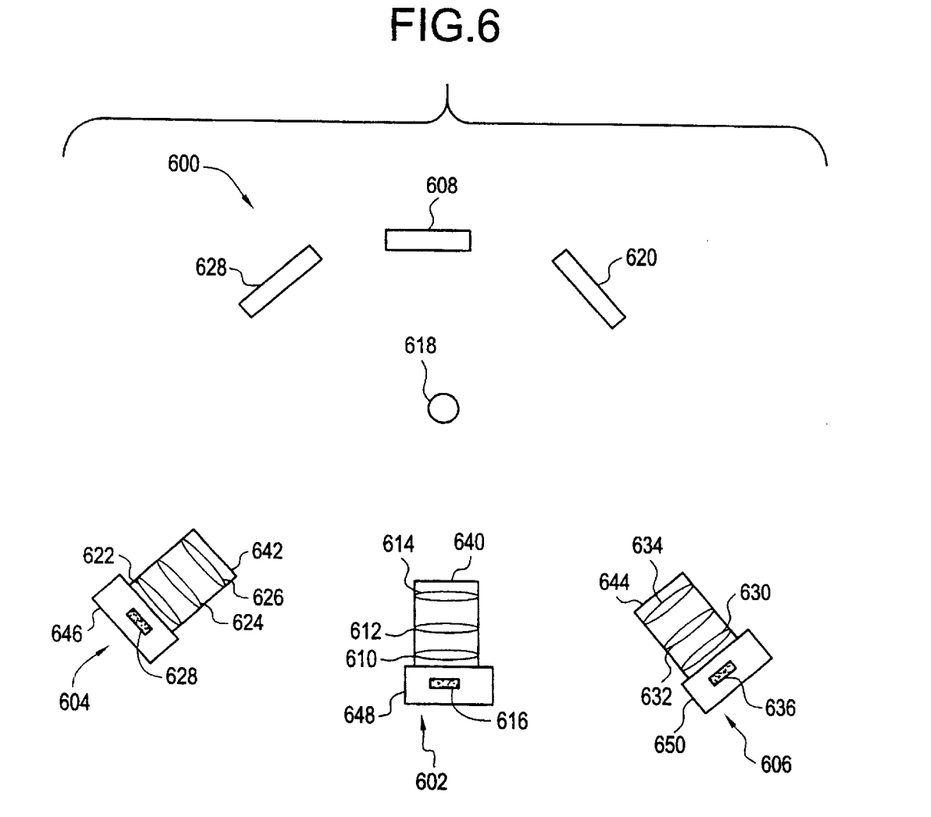
FIG. 6 is a three-view flash-detection system according to the present invention.

FIG. 6 provides a top view of a three-view detection system 600. The detection system 600 may also suitably be used as the flaw detector 12 of FIG. 1. The detection system 600 includes view systems 602, 604 and 606. It is presently preferred that each of the view systems 602, 604, and 606 be located an equal distance from the fiber 314. The view system 602 includes spherical mirror 608, first, second and third lenses 610, 612 and 614, respectively, and a first detector 616. A concave mirror, with a focal distance, f=25 mm, part number 44351 from Oriel Corp. may suitably be used as the mirror 608. Suitable choices for the first, second and third lenses 610, 612 and 614, respectively, are Bi-Convex lens, f=25.4 mm, Part number KBX046AR.14, Bi-Convex lens, f=50.2 mm, Part number KBX142AR.14, and Piano-Convex lens, f=6.4 mm, Part number KPX010AR.14, respectively, all from Newport Corporation. A suitable choice for the first detector 616 is Detector/Amplifier Package, Part Number PDA50, from Thorlabs. Mirror 608 is placed at its radius of curvature away from fiber 618. Third lens 614 is placed in a straight line from mirror 608 and fiber 618, on the opposite side of fiber 618 from mirror 608, at a distance from the fiber 618 of the focal length of the lens 614. Lens 612 is placed in a straight line with mirror 608, fiber 618 and lens 614, on the opposite side of lens 614 from fiber 618. Lens 610 is placed in a straight line with mirror 608, fiber 618 and lenses 614 and 612, on the opposite side of lens 612 from lens 614. Lenses 610 and 612 are preferably spaced 17.8 mm apart. Detector 616 is placed in a straight line with mirror 608, fiber 618 and lenses 614, 612 and 610, on the opposite side of lens 610 from lens 612, at a distance from lens 610 of the focal length of lens 610. Lenses 610,612 and 614 are suitably mounted in a lens mount 640 which is preferably adapted to fit directly into a housing 646 for the detector 616. This arrangement operates to shield the detector 616 from ambient light which may have entered the detection system 600.

View system 604 is oriented in a straight line which intersects the fiber 618, 60 degrees from the view system 602, in the same plane as view system 602. View system 604 includes second spherical mirror 620, fourth, fifth and sixth lenses 622, 624 and 626, respectively, and a second detector 628. Mirror 620 is placed at its radius of curvature away from fiber 618. Sixth lens 626 is placed in a straight line from mirror 620 and fiber 618, on the opposite side of fiber 618 from mirror 620, at a distance from fiber 618 of the focal length of lens 626. Lens 624 is placed in a straight line with mirror 620, fiber 618 and lens 626, on the opposite side of lens 626 from fiber 618. Lens 622 is placed in a straight line with mirror 620, fiber 618 and lenses 626 and 624, on the opposite side of lens 626 from lens 624. Detector 628 is placed in a straight line with mirror 608, fiber 618 and lenses 626, 624 and 622, on the opposite side of lens 624 from lens 622, at a distance from lens 622 of the focal length of lens 622. Lenses 622, 626 and 624 are suitably mounted in a lens mount 642 which is preferably adapted to fit directly into a housing 648 for the detector 628. This arrangement operates to shield the detector 628 from any ambient light which may have entered detection system 600.

View system 606 is oriented in a straight line which intersects the fiber 618, 60 degrees from view system 602 in the opposite direction from view system 604, in the same plane as the view systems 602 and 604. View system 606 includes spherical mirror 628, seventh, eighth and ninth lenses 630, 632 and 634, respectively, and third detector 636 which are located, mounted and housed similarly to the corresponding components of the view systems 602 and 604. The parts listed above as suitable in the description of the first view system 602 are also suitably used for the corresponding parts in the second view system 604 and the third view system 606.

Detection system 600 is preferably enclosed in a light-tight enclosure with suitable entry and exit points for fiber 618, with baffles shielding these entry and exit points. The light-tight enclosure of detection system 600 is not shown, but may be similar to those described above in conjunction with the embodiments of FIGS. 2B and 3.

The three-view system 600 eliminates the dead zone to which the two-view detector system 300 of FIG. 3 is subject. Moreover, through an appropriate selection of the components such as those listed above, the three-view system may be constructed so as to maximize the time that a flash is in the field of view, thereby facilitating flash detection at high speeds, such as typical draw speeds.

Figure 7:
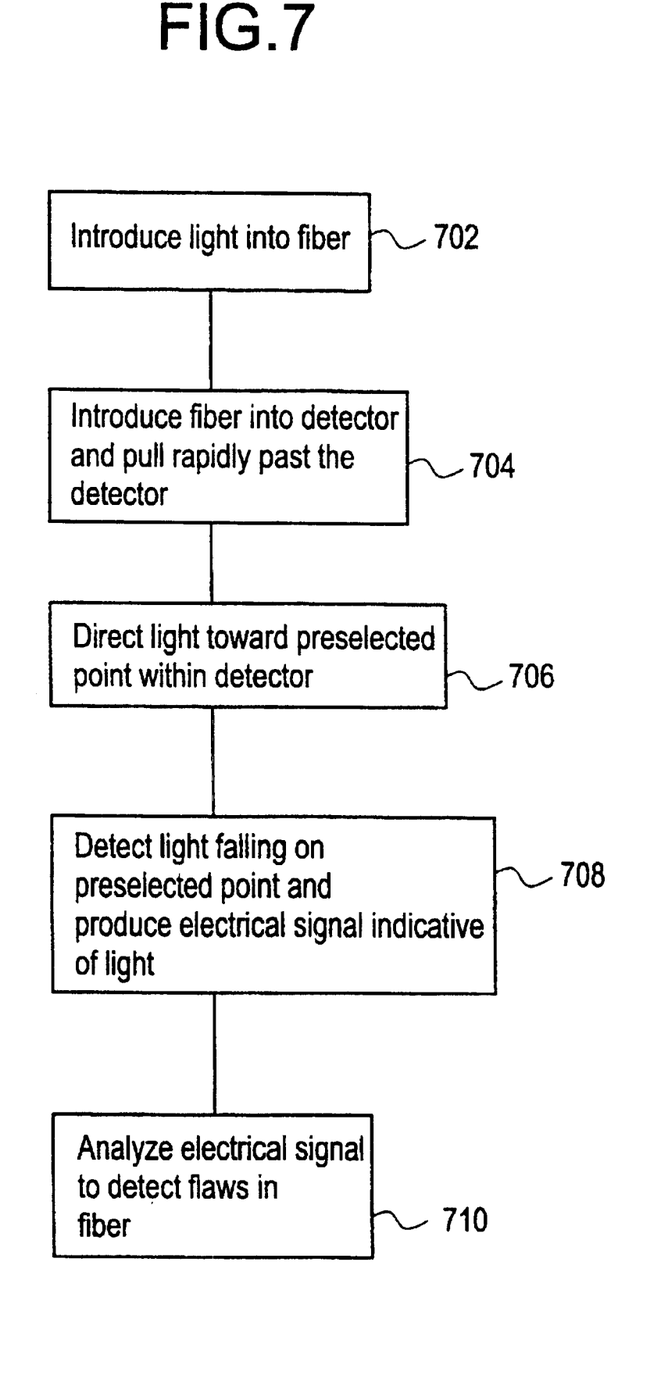
FIG. 7 illustrates a method of flash detection in accordance with the present invention.

FIG. 7 is a flowchart illustrating a process of flash detection 700 according to the teaching of the present invention. At step 702, light is introduced into an optical fiber, such as the fiber 1 of FIG. 1 which is filled by light in the draw furnace 11. At step 704, the fiber is introduced into and pulled rapidly past a detector, the detector preferably comprising mirrors, lenses, or other optical devices, as well as, detection circuitry for detecting light as the fiber is rapidly moving by a predetermined point. The fiber continues in motion through the detector, enabling the entire fiber to pass through the detector and light escaping at any point along the length of the fiber is detected making the process highly suitable for real time testing during the manufacturing process. As addressed above, the detector elements are preferably contained within a substantially light-tight enclosure. At step 706, light escaping from the fiber is directed to a desired point within the detector. At step 708, light falling on the desired point is detected and an electrical signal representative of that light is produced. Finally, in step 710, the electrical signal is processed and analyzed to defect fiber flaws. A data processing and analysis system, such as the data acquisition system 20 of FIG. 1, may be employed to analyze the signal and to distinguish one type of flaw from another. Records of the detected flaws may be stored in memory, printed on a chart recorder, such as the recorder 30 of FIG. 1, or displayed on a display.

While the present invention is disclosed in the context of a presently preferred embodiment, it will be recognized that a wide variety of implementations may be employed by persons of ordinary skill in the art consistent with the above discussion and the claims which follow below.

We claim:

1. An optical fiber flaw detection system for detecting white light emitted through a sidewall of an optical fiber as a result of particle on glass flaws or abrasions in the optical fiber, the detection system operating as the optical fiber is drawn through the detection system, the system comprising:

a detector located adjacent to the optical fiber and prior to a coating system, the detector operating to detect emitted white light; and processing circuitry to amplify and convert a signal produced to recognize flaws.

2. The flaw detection system of claim 1 further comprising an optical assembly for collecting the emitted light and directing it onto the detector.

3. The flaw detection system of claim 1 wherein the optical assembly includes an elliptical mirror, the elliptical mirror having two foci.

4. The flaw detection system of claim 3, in which the fiber is rapidly drawn through one of the foci of the elliptical mirror.

5. The flaw detection system of claim 4, in which the detector is positioned at the other of the foci of the elliptical mirror.

6. The flaw detection system of claim 5, in which the mirror and the detector are enclosed within a substantially light-tight enclosure.

7. The flaw detection system of claim 6 further comprising entry and exit holes in the light-tight enclosure for allowing the optical fiber to pass through the detection system and baffles around said holes to minimize admission of stray light into the detection system.

8. The flaw detection system of claim 1 further comprising a white light source above said detector.

9. The flaw detection system of claim 1 wherein a source of the white light comprises a white hot preform.

10. The flaw detection system of claim 1 wherein the fiber comprises an uncoated fiber.

11. A method of detecting optical fiber flaws which cause white light to escape from a sidewall of an optical fiber, said method comprising the steps of:
   introducing white light into the fiber;
   introducing the fiber into a detector assembly;
   detecting white light which escapes from a sidewall of the fiber utilizing the detector assembly; and
   determining on-line the nature of the flaw based upon the detected white light.

12. The method of claim 11 further comprising drawing the fiber from a source of white light.

13. The method of claim 11 wherein said detecting step occurs prior to applying a coating the fiber.

14. A system for the detection during the optical fiber draw process of optical fiber particle or glass flaws other than holes, the system comprising:
   an optical detector located subsequent to a draw furnace and before a coating system, and arranged to detect emitted white light; and
   a data acquisition system to analyze detected white light and to recognize optical fiber flaws other than holes.

15. The system of claim 14 further comprising an optical assembly for collecting emitted light and directing it to the optical detector.

16. The system of claim 14 further comprising an optical fiber hole detector connected to the data acquisition system.

17. The system of claim 14 further comprising an alarm and wherein the data acquisition system activates the alarm if a predetermined number of particle on glass flaws are detected.

18. An optical fiber flaw detection system for detecting white light emitted through a sidewall of an optical fiber resulting from flaws in the optical fiber, comprising:
   a plurality of view systems oriented about said optical fiber, each view system comprising:
      an optical assembly for collecting and directing white light emitted from the optical fiber; and
      a detector placed to receive light directed by the optical assembly and located before a coating system; and
      a mechanism for rapidly drawing the optical fiber through the plurality of view systems.

19. The flaw detection system of claim 18 in which at least one of said optical assemblies comprises:
   a spherical mirror having a radius of curvature, said mirror being placed at its radius of curvature distant from the optical fiber;
   a first lens having a first focal length, the first lens being placed in a line with the mirror and the fiber, at the opposite side of the fiber from the mirror, at the first focal length distant from the optical fiber; and
   a second lens having a second focal length, the second lens being placed in a line with the first lens, the fiber and the mirror, at the opposite side of the first lens from the fiber.

20. The flaw detection system of claim 19, in which the number of view systems is three.

21. The flaw detection system of claim 20, in which the view systems are placed in the same plane with one another at an orientation of 60 degrees from one another.

22. The flaw detection system of claim 19, in which each view system also includes a third lens between the first lens and the second lens.

23. The flaw detection system of claim 18, in which the number of view systems is two.

24. The flaw detection system of claim 23, in which the view systems are placed in the same plane with one another at an orientation of 90 degrees from one another.

25. The flaw detection system of claim 18 further comprising a difference circuit for producing a difference signal representing the difference between outputs of at least two of said plurality of view systems.

26. The optical fiber flaw detection system of claim 18 further comprising:
   a light-tight enclosure enclosing the plurality of view systems and the fiber, the light-tight enclosure having holes for entry and exit of the fiber; and
   baffles covering the holes in the light-tight enclosure to prevent entry of stray light into the light-tight enclosure.

27. The flaw detection system of claim 18 further comprising a white light source located before said detector.

28. The flaw detection system of claim 18 wherein a source of the white light comprises a white hot preform.

29. The flaw detection system of claim 18 wherein the fiber comprises an uncoated fiber.

30. A method of detecting optical fiber flaws which cause light to escape from a sidewall of an optical fiber, said method comprising:
   heating a preform to a temperature sufficient to draw fiber from the preform,
   said temperature sufficient to transmit white light along the fiber;
   drawing the fiber from the preform; and
   detecting white light which escapes from a sidewall of the fiber.

31. The method of claim 30 further comprising purging at least one surface of a detector assembly.

32. The method of claim 30 further comprising preventing ambient light from entering a detector assembly.

33. The method according to claim 30 wherein said detecting comprises collecting the white light which escapes from the fiber and directing the light onto a rod, thereby producing a fluorescent light.

34. The method according to claim 33 further comprising detecting the fluorescent light.

35. The method according to claim 30 further comprising determining on-line the nature of the flaw based upon the detected light.

36. The method according to claim 30 wherein said heating comprises heating the preform white hot.

* * * * *